United States Patent [19]

Mann et al.

[11] Patent Number: 5,031,616
[45] Date of Patent: Jul. 16, 1991

[54] IMPLANTABLE STIMULATION DEVICE HAVING MEANS FOR SELF-REGULATING CURENT DRAIN USAGE AT BATTERY DEPLETION

[75] Inventors: Brian M. Mann, Los Angeles; John W. Poore, South Pasadena, both of Calif.

[73] Assignee: Siemens-Pacesetter, Inc., Sylmar, Calif.

[21] Appl. No.: 448,191

[22] Filed: Dec. 7, 1989

[51] Int. Cl.⁵ ............................................. A61N 1/378
[52] U.S. Cl. ........................ 128/419 PG; 128/419 PS
[58] Field of Search .................... 128/419 PS, 419 PT, 128/419 PG

[56] References Cited

U.S. PATENT DOCUMENTS

| | | | |
|---|---|---|---|
| 3,474,353 | 10/1969 | Keller | 331/113 |
| 3,825,016 | 7/1974 | Lale et al. | 128/419 P |
| 3,901,247 | 8/1975 | Walmsley | 128/419 PG |
| 4,120,307 | 10/1978 | Jirak et al. | 128/419 PT |
| 4,230,120 | 10/1980 | McDonald | 128/419 PT |
| 4,237,897 | 12/1980 | Beane et al. | 128/419 PG |
| 4,390,020 | 6/1983 | Herpers | 128/419 PG |
| 4,535,774 | 11/1985 | Olson | 128/419 PG |
| 4,590,941 | 5/1986 | Saulson et al. | 128/419 PG |

Primary Examiner—William E. Kamm
Attorney, Agent, or Firm—Lisa P. Weinberg; Leslie S. Miller

[57] ABSTRACT

A system within an implantable stimulation device and a method for limiting the extent to which any high power consumption modes, such as a rate response mode, can be utilized during low battery periods. A battery threshold detector is utilized to detect when the battery is below a predetermined threshold. The implantable stimulation device then switches from a high current drain mode of operation to progressively lower current drain modes of operation. This configuration allows a significant reduction in current drain at RRT and further prevents the output amplitude from dropping below the capture level and prevents the remaining battery capacity from being rapidly used up.

23 Claims, 5 Drawing Sheets

IMPLANTABLE STIMULATION DEVICE HAVING MEANS FOR SELF-REGULATING CURENT DRAIN USAGE AT BATTERY DEPLETION

BACKGROUND OF THE INVENTION

Field of the Invention

The present invention relates generally to implantable cardiac pacemakers, and more specifically to rate responsive pacemakers wherein the upper rate is limited as the battery approaches its end-of-life (EOL). In alternative embodiments, the invention can be used with any high power consumption features within an implantable device to extend the longevity of the battery by limiting the extent to which these features may be utilized.

Implantable cardiac pacemakers are powered by a battery within the pacemaker housing. Once implanted, it is difficult to determine the battery's state of depletion and, thus, the need for replacement. Although the surgery required for replacement is relatively minor, the associated risks of complications to the patient are ever present. In general, it is considered better to avoid replacement of a properly functioning pacemaker until absolutely necessary.

To determine when to explant a pacemaker prior to its EOL, physicians plan their follow-up schedules less frequently during the battery's "beginning-of-life" (BOL) and more frequently towards the battery's recommended replacement time (RRT) and the battery's "end-of-life" (EOL). (EOL is defined as the point in time in which the pacemaker pulse amplitude is reduced to approximately 50 percent of the programmed value.) As the basis, physicians estimate the remaining battery capacity by subtracting the "nominal" current drain of the pacemaker, usually specified at 5 volts with 100% pacing at a rate of 70 pulses-per-minute (ppm), from the theoretical available amp-hour capacity of the battery. Even though accurate battery capacity sensors have been developed (see, for example, U.S. Pat. No. 4,556,061 to Barreras et. al.), the physician must still accurately predict the power consumption for the remaining period. With sophisticated pacemakers and unpredictable current drain modes of operation, physicians have to schedule more frequent follow-up visits to accurately monitor the replacement time and still avoid premature surgical replacement.

Current drain on a battery is largely dictated by the pacer output amplitude, pulse width, and rate. Programmability of these pacemaker parameters offers some flexibility to safely prolong the longevity of the battery. For example, it is well known that the battery life can be increased anywhere from 3 to 9 months by programming the rate to 70 instead of 90 beats-per-minute (bpm). However, not all patients can tolerate being paced at 70 bpm. Active patients need a higher rate during exercise. In patients with a normal sinus node, higher rates may be achieved with a dual chamber pacemaker, wherein the atrial rate is sensed and the ventricles are stimulated a short delay later (mimicking a normal heart). During exercise, the atrial rate may vary between 70 and 120 bpm or more. It is also known that rate responsive pacemakers can increase the pacing rate according to an additional sensor (accelerometer or "activity" sensor, oxygen saturation, QT measurements, respiration rate, temperature, etc.). The purpose of such pacemakers is to accelerate the rate when the atrium is incompetent, that is, non-responsive to exercise stress or prone to atrial flutter or fibrillation.

In both of these pacemakers, the amount of current drain on the battery can change quite rapidly as the pacing rate of the pacer may change from a low rate to a high rate. This is especially true where the patient's own intrinsic rhythm is able to sustain the patient's needs at low activity levels (a low current drain condition), but where stimulated pacing is required in one or both chambers of the heart at a high activity level (a high current drain condition). Unfortunately, such large variations in current drain can cause a sudden battery voltage drop below the EOL voltage level such that the possibility exists that the battery voltage could drop low enough to cause loss of capture. Furthermore, if pacing occurs at fast rates, such as occurs during exercise, the increase in current drain could dramatically reduce or even eliminate the safety margin associated with the last reported recommended replacement time (RRT) of the pacer, particularly when the last reported RRT is based on the current drain while the patient was at the rest rate.

It is also known in the art (see for example, U.S. Pat. No. 4,686,988 to Sholder) that battery current drain due to the delivered pacing pulse can be reduced by automatically adjusting the output amplitude and/or pulse width of the pacing pulse such that the lowest possible output is delivered which can still stimulate or "capture" the heart. This feature does ensure that the patient will not lose capture throughout the life of the pacemaker, however, this increase in processing time of the microprocessor and the constant changing of the output amplitude and/or pulse width introduces still more variables to consider when determining the replacement time of the pacemaker.

Furthermore, with the advent of microprocessor-based pacemakers, functionality has been extended to automatic adjustment of pacemaker parameters, storing and telemetering of intracardiac electrograms (EGMs), processing multiple sensors, detecting and breaking arrhythmias and recognizing waveform patterns. The current drain of the pacemaker may also be significantly influenced by the duty cycle of the microprocessor in performing these functions. Without careful monitoring of the battery voltage, these high current drain situations may cause a temporary drop in available battery voltage, increase the risk of loss of capture, and dramatically use up the remaining battery capacity.

What is needed is a pacemaker which can regulate its own current drain usage, conserve the limited battery energy towards EOL, prevent loss of capture by limiting high current drain modes, and ultimately eliminate premature replacement of the pacemaker by eliminating the unpredictable nature of the RRT to EOL interval. Furthermore, this pacemaker should not burden the physician by increasing the number of follow-up visits near EOL.

SUMMARY OF THE INVENTION

The disadvantages and limitations of the background art discussed above are overcome by the present invention. The present invention may be used to limit power consumption as the battery approaches and exceeds the RRT. The present invention is capable of selectively altering operating parameters, based on a predetermined priority, to provide the longest possible active life for the pacemaker, while still providing a good quality of life as required by the patient's physiological needs. These actions help conserve the limited remaining battery energy and prevent loss of capture.

The present invention includes an implantable cardiac device having conventional components including a battery, a pulse generator for generating stimulating pulses, sense amplifiers for sensing cardiac signals, and a timing and control means. The device also includes a battery threshold detector for detecting a predetermined threshold level of the battery, having a high current drain mode of operation and at least two successively lower current drain modes of operation, and a processing means for switching to a successively lower current drain mode each time the battery threshold detector indicates that the battery voltage is below a prescribed threshold. This configuration allows a significant reduction in current drain.

In the preferred embodiment, the implantable cardiac device is a rate responsive pacemaker. Instead of simply reporting the battery voltage upon interrogation of the pacemaker or completely disabling functions, as is done in the prior art, the pacemaker will automatically regulate its current drain usage by limiting the pacing rate to a value less than the sensor-indicated rate. This is achieved by continuously monitoring the battery voltage for the occurrence of a voltage at or below the predetermined threshold during rate responsive pacing. If such a voltage is detected, the allowable maximum sensor rate is automatically reduced (which, in turn, reduces the battery current drain). This new allowable maximum sensor rate remains in effect until the battery voltage is above the predetermined threshold or until the allowable maximum sensor rate is otherwise reset. As the battery continues to deplete, the allowable maximum sensor rate will eventually reduce the pacing rate to the programmed rest rate, or "base" rate, effectively disabling rate responsive pacing. In an alternative embodiment, the rate could even go lower than the rest rate.

In effect, the pacemaker is switching from a high current drain mode (rate responsive pacing at a high rate), to a lower current drain mode (rate responsive pacing at successively lower rates) until the battery voltage is above the predetermined threshold. In yet another embodiment, the invention controls the extent to which other high current drain modes can be utilized by the pacemaker once the predetermined threshold has been reached.

The invention described herein further contemplates a method for maintaining output amplitude at battery depletion by self-regulating current drain usage. In one embodiment, this is achieved by reducing the rate of a rate responsive pacemaker when the battery voltage reaches a predetermined threshold value. In a second embodiment, the pacemaker is switched from a high current drain mode to a successively lower current drain mode until the battery voltage is above the predetermined threshold.

As such, the present invention does not require an increase in physician follow-up as the battery approaches RRT. Rather, its self-regulation of high current drain features allows the same follow-up schedule as VVI pacemakers with an increase in reliability and confidence.

Finally, all of the problems and disadvantages of the prior art are overcome in the present invention without incurring any substantial relative disadvantage. It will therefore be perceived that the advantages of the present invention result in extending the longevity of the pacemaker while providing a high quality of life for the patient for as long as possible, making the method of the present invention a highly desirable enhancement to implantable cardiac pacemaker therapy.

DESCRIPTION OF THE DRAWINGS

The features and other advantages of the present invention may be more readily understood by reference to the following description taken in conjunction with the accompanying drawings, in which.

DETAILED DESCRIPTION OF THE PREFERRED EMBODIMENT

The present invention may easily be understood with reference to FIG. which shows the estimated discharge characteristics of a lithium iodide battery cell as is commonly used in many pacemakers today. These cells may be characterized as a fixed voltage source, with a stable open circuit voltage and an internal impedance which increases over time. Therefore, the available terminal voltage will vary inversely with the current drain from the battery, due to the internal voltage drop across the internal cell impedance.

Figure 1:
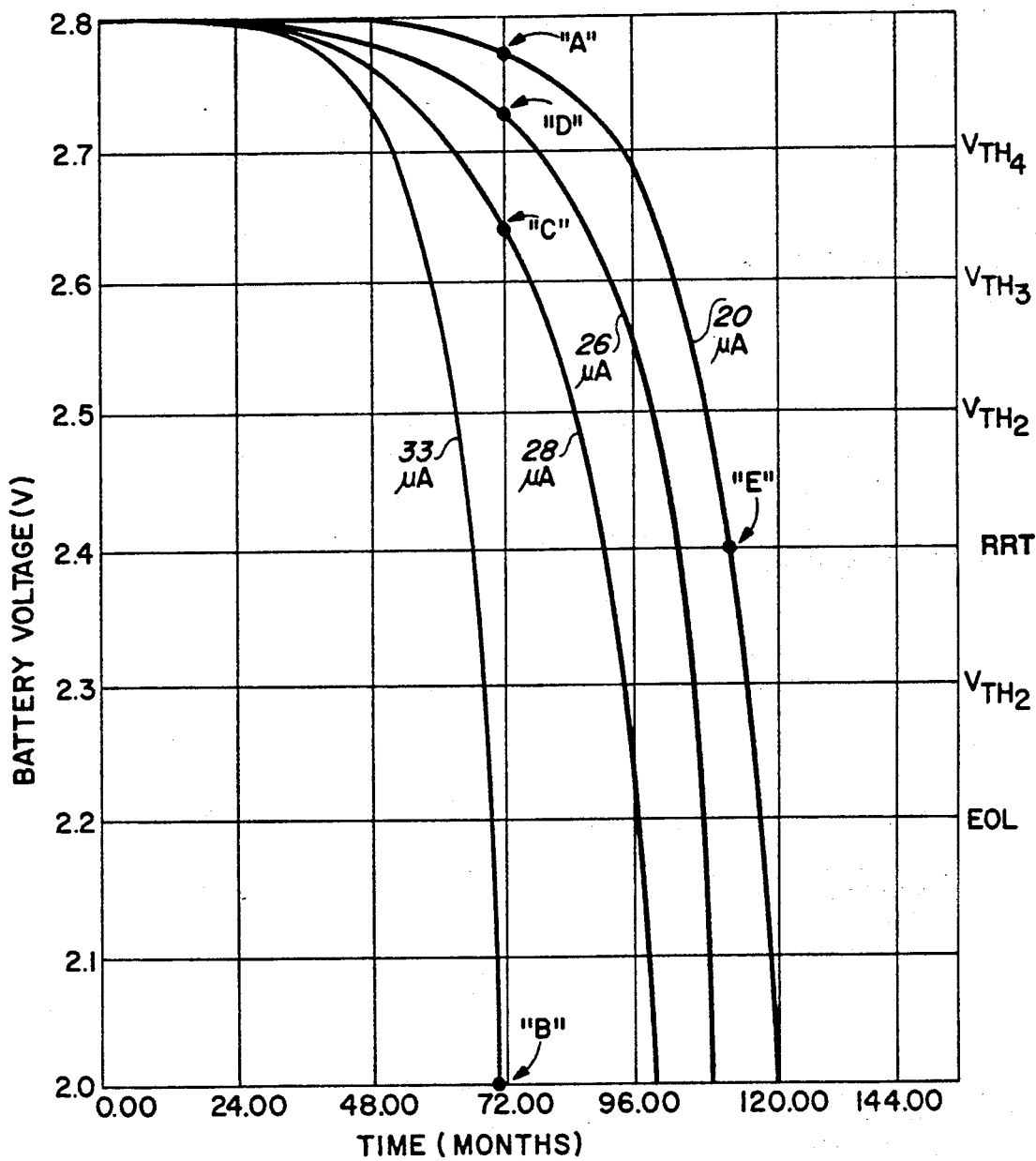
FIG. 1 shows the projected discharge characteristics of a typical lithium iodide battery.

As mentioned previously, the current drain is significantly influenced by the rate at which the pacemaker is delivering stimulating pulses. Point "A" in FIG. 1 represents a patient with a rate responsive pacemaker wherein the patient is resting, therefore the current drain is low, say, at 20 uA. If the patient should suddenly need a high increase in rate, the current drain may increase to, say, 33 uA, and the available battery voltage would drop to 2.0 volts as indicated at point "B". It can therefore be seen that this increase in rate can cause a sudden battery voltage drop below the EOL voltage level such that the possibility exists that the battery voltage could drop low enough to cause loss of capture. By limiting the pacing rate such that the current drain was only 28 uA, the available battery voltage would rise to point "C", clearly well above the RRT threshold. A further reduction in the pacing rate, would enable the available battery voltage to rise to point "D" with an even greater safety margin.

It can further be easily seen in FIG. 1 that the remaining time to EOL is significantly increased as the operating point moves from point "B" to points "C", "D", and ultimately to "A". Once the battery terminal voltage reaches RRT at point "E", and the current drain cannot be reduced any further, the pacing rate is set to the Base Rate (or rest rate) and rate responsive pacing is effectively suspended.

Figure 2A:
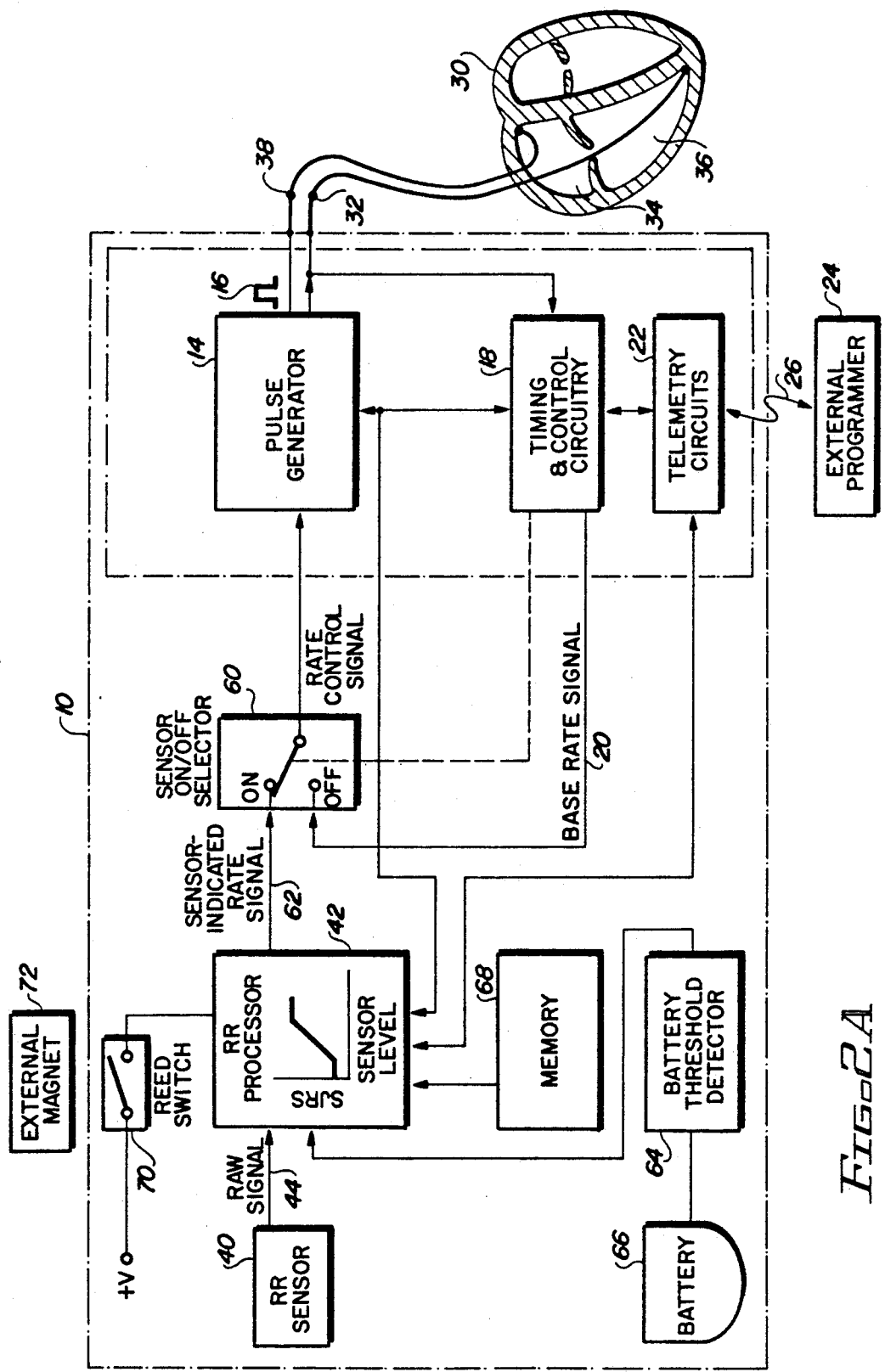
FIG. 2A is a block diagram of the present invention configured within a rate responsive pacemaker.

A block diagram of the present invention, coupled to a rate responsive pacer, is shown in FIG. 2A. A complete description of the rate responsive pacemaker is included in copending U.S. Pat. No. 4,940,053 entitled "Energy-controlled Rate-responsive Pacemaker Having Automatically Adjustable Control Parameters", and U.S. Pat. No. 4,940,052 entitled "Micro-Controlled Rate Responsive Pacemaker Having Automatic Rate Response Threshold Adjustment". These patents are assigned to the same assignee as is the present application, and these two copending patents are hereby incorporated herein by reference.

Briefly, the rate responsive pacemaker functions as follows. The pacemaker 10 includes a conventional pacemaker chip 12 which has a pulse generator 14 for generating stimulating pulses 16 to the heart 30. Sense amplifiers (not shown) are employed to sense cardiac events and to communicate this information to timing and control circuitry 18. The timing and control circuitry 18 controls a base rate signal 20 for the pulse generator 14 and controls the inhibition of a stimulus in the event of a sensed cardiac signal. Telemetry circuits 22 are connected electrically to the timing and control circuitry 18. An external programmer 24 is used to noninvasively send programming signals to the telemetry circuits 22. These programming signals are depicted symbolically as the wavy line 26 in FIG. 2A. It is noted that such signals may be sent bi-directionally between the external programmer 24 and the pacemaker 10. In this way the external programmer 24 can noninvasively alter the pacemaker's programmable parameters.

A more complete description of the pacemaker operation may be found in several patents. For example, note U.S. Pat. No. 4,232,679 to Schulman, entitled "Programmable Human Tissue Stimulator"; U.S. Pat. No. 4,686,988 to Sholder, entitled "Pacemaker System and Method for Measuring and Monitoring Cardiac Activity and for Determining and Maintaining Capture"; and U.S. Pat. No. 4,809,697 to Causey et.al., entitled "Interactive Programming and Diagnostic System for Use with an Implantable Pacemaker". While not disclosing the exact same pacemaker chip 12 or circuits which are used in the preferred embodiment of the present invention, these patents nonetheless disclose the primary components of a conventional pacing system and teach the basic operation thereof. U.S. Pat. No. 4,232,679; U.S. Pat. No. 4,686,988, and U.S. Pat. No. 4,809,697 are hereby incorporated herein by reference.

In the preferred embodiment, the pulse generator 14 is connected electrically to the patient's heart 30 via a lead 32. Alternatively, the pulse generator 14 may be connected to the atrium 34 and the ventricle 36 via two leads 32 and 38, respectively. These leads 32 and 38 may be either unipolar leads, bipolar leads, or other multipole leads, all of which are known in the art.

The pacemaker 10 further includes a rate responsive sensor 40 for sensing the physiological needs of the patient. In the preferred embodiment, the rate responsive sensor 40 is a piezoelectric sensor which detects physical activity. However, the present invention is not restricted to this type of sensor and could be used with any of the known rate responsive sensors (QT, temperature, oxygen saturation, impedance, pre-ejection period (PEP), minute volume, accelerometers, etc.). Since the invention described herein is independent of the type of sensor, hereinafter the sensor which is used to change the pacing rate shall simply be referred to as the "RR sensor". Furthermore, although the RR sensor 40 is shown in FIG. 2A as being included within the pacemaker 10, it is to be understood that the RR sensor 40 could also be included within, or coupled to, the leads 32 and 38, or otherwise placed external to the pacemaker 10.

Figure 2B:
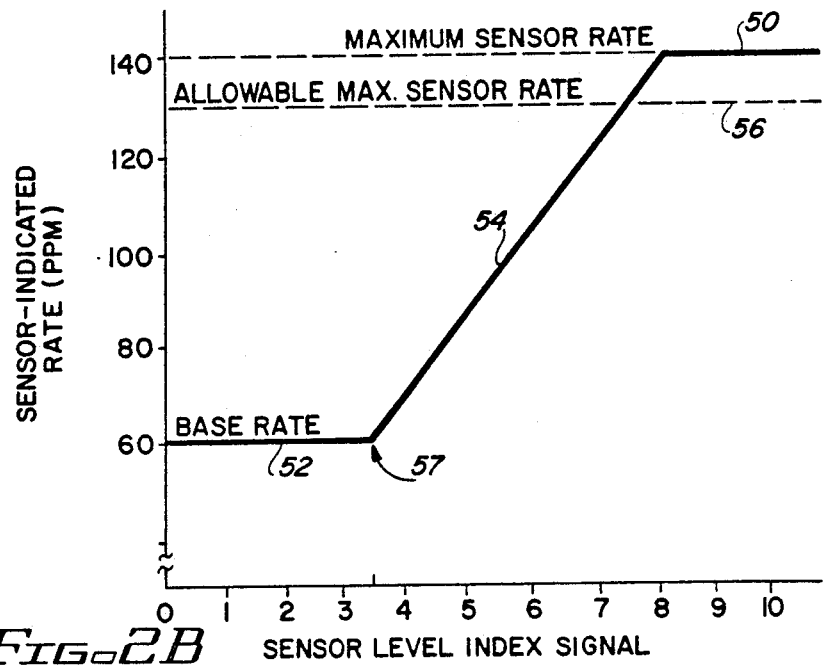
FIG. 2B is a transfer curve for the rate response processor shown in FIG. 2A.

In the preferred embodiment, the output of the RR sensor 40 is measured during each pacing cycle by the RR processor 42. Typically, the RR processor 42 includes means for converting the raw signal 44 to a sensor-indicated rate signal 62. In the preferred embodiment, the sensor-indicated rate signal 62 is based on the energy content of the raw signal 44. The conversion may be accomplished in several ways, using conventional techniques: typically by a transfer curve, look-up table (stored or programmed into the memory 68), algorithmically, or in hardware, software or a combination thereof. The preferred transfer curve is shown in FIG. 2B, wherein the physician may program a Maximum Sensor Rate (MSR) 50, a Base Rate 52 (or minimum rate), and the slope 54 and threshold 57 therebetween. Based on the energy content (x-axis), a sensor-indicated rate may be determined.

In operation, the rate responsive pacer may operate in either a SENSOR ON mode or a SENSOR OFF mode which can be selected by an appropriate programming signal received from the external programmer 24. A switch 60 is employed to select either the base rate signal 20 (during SENSOR OFF mode) determined by the timing and control circuitry 18 or the sensor-indicated rate signal 62 (during SENSOR ON mode) determined by the RR processor 42.

A battery threshold detector 64, connected to a battery 66, is used to detect a voltage above or below a predetermined threshold. In the preferred embodiment, the predetermined threshold is the result of an impedance level detected at RRT, however, other threshold levels may be contemplated without deviating from the basic teaching of the invention. If the pacemaker 10 is pacing at an elevated rate due to exercise or stress and the battery 66 is at or below the RRT threshold level, then the battery threshold detector 64 triggers the RR processor 42 to decrease the current pacing rate by a small amount. This decreasing of the pacemaker rate will continue until the battery 66 is above the RRT threshold, or until the current rate reaches the Base Rate. In an alternative embodiment, the decreasing of the pacemaker rate will continue until the battery 66 is above the RRT threshold, or until the current rate reaches a rate lower than the Base Rate. This reduction of pacing rate at RRT ensures that the remaining replacement time before EOL will not be rapidly used up, capture will be maintained, and that rate responsive modes can be utilized for as long as possible.

Figure 3:
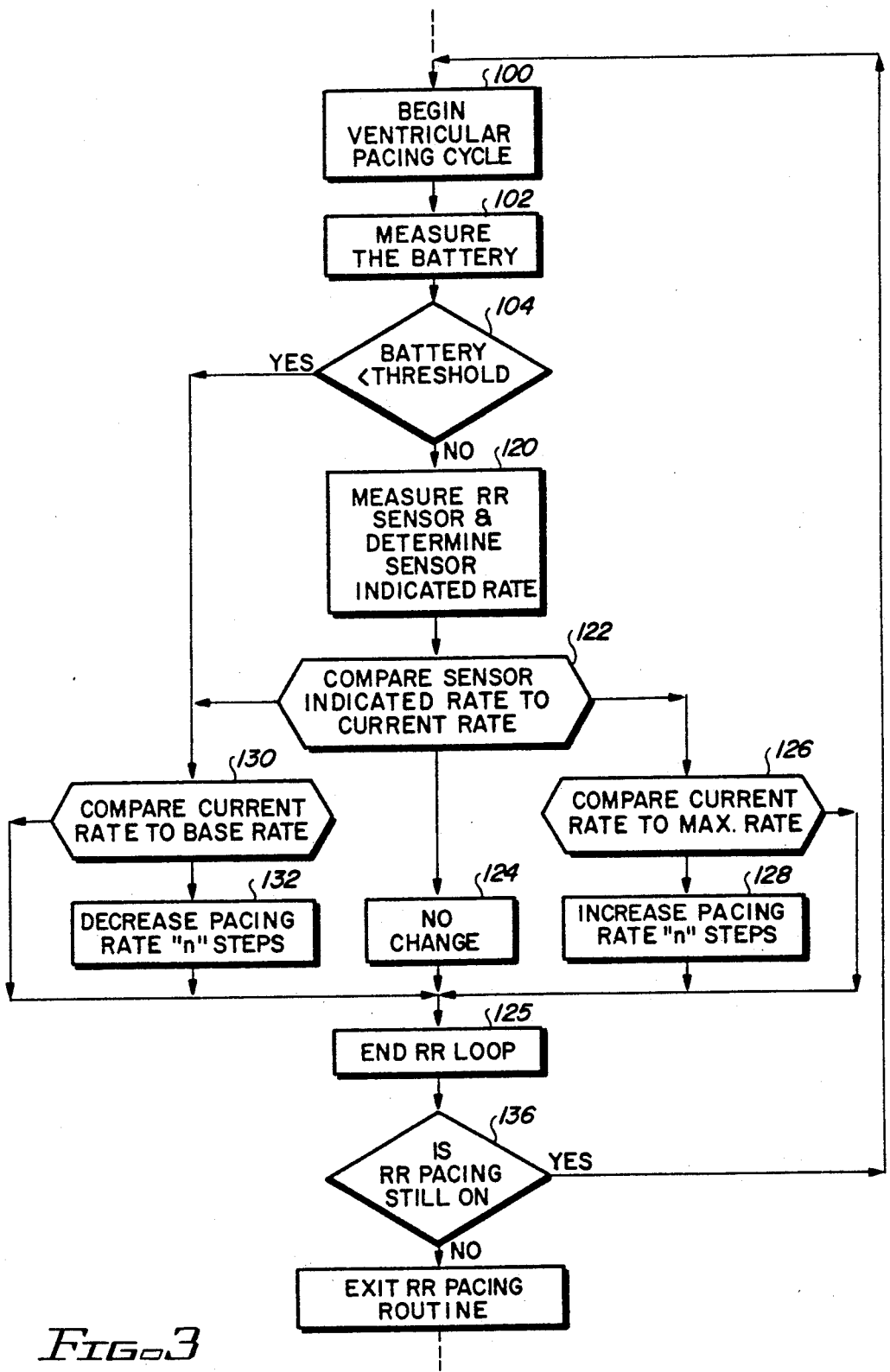
FIG. 3 is a diagram which teaches the basic principles of the method for maintaining output amplitude at battery depletion in the rate responsive processor shown in FIG. 2A.

In FIG. 3, a method for maintaining output amplitude at battery depletion is shown. A ventricular pacing cycle is initiated at 100. Following the stimulus, the battery is measured at 102. The battery voltage is compared to a predetermined threshold at step 104. If the battery voltage is above the predetermined threshold, then the RR sensor is measured and the sensor-indicated rate is determined at 120.

At 122, the sensor-indicated rate is compared to the current rate: if they are equal, no change in rate is initiated at 124 and the rate response loop ends at 125. If the sensor-indicated rate is greater than the current rate, then the current rate is compared to the (programmed) Maximum Sensor Rate at 126. If they are equal, no change in rate is initiated and the rate response loop ends at 125. If the current rate is below the (programmed) Maximum Sensor Rate, then the pacing rate is incremented by "n" steps at 128. In the preferred embodiment, "n" equal 1 step.

If the sensor-indicated rate is less than the current rate (and the battery is above the predetermined threshold) or if the battery is at or below the predetermined threshold, then the current rate is compared to the Base Rate at 130. If the current rate is equal to the Base Rate, the rate response loop ends at 125. If the current rate is above the Base Rate, then the pacing rate is decremented by "n" steps at 132. Finally, control will loop back to repeat the pacing cycle at 100, providing that rate responsive pacing has not been turned off at 136.

In the preferred embodiment, an "allowable" maximum sensor rate (AMSR) is used to provide an intermediate rate limit based on battery measurements detected below threshold. As shown in FIG. 2B, the Allowable Maximum Sensor Rate (AMSR) 56 is adjustable between the Base Rate 52 and the (programmed) Maximum Sensor Rate (MSR) 50. Briefly, with reference to FIG. 2A, each time the battery 66 is below threshold, the RR processor 42 decreases the current rate by at least one 1 step and sets the AMSR to the new current rate. The AMSR can be stored in a counter within RR processor 42 or external to it or at a location within memory 68. The AMSR will continue to be decremented until the RR processor 42 detects at least two consecutive battery measurements above threshold or until the current rate reaches the Base Rate. When the former instance occurs, the AMSR is permitted to increment back towards the programmed Maximum Sensor Rate. These additional features enable greater rate responsiveness for the patient by preventing a single occurrence of a low battery detection to cause the pacemaker to permanently restrict the rate.

If the current rate remains at the Base Rate for 255 beats, the rate responsive mode will be suspended until a magnet 70 is applied to reset a reed switch 72 in the pacemaker 10 (FIG. 2A). This additional feature enables greater rate responsiveness for the patient by preventing a single occurrence of the current rate being equal to the Base Rate from disabling the rate response mode.

In the preferred embodiment, the pacemaker 10 will not automatically return to rate responsive pacing immediately upon reset of the reed switch 70. Instead, the pacemaker waits for a programming command from the physician via the external programmer 24. This feature allows the physician sufficient time to determine the status of the battery before re-enabling the rate responsive mode.

Figure 4B:
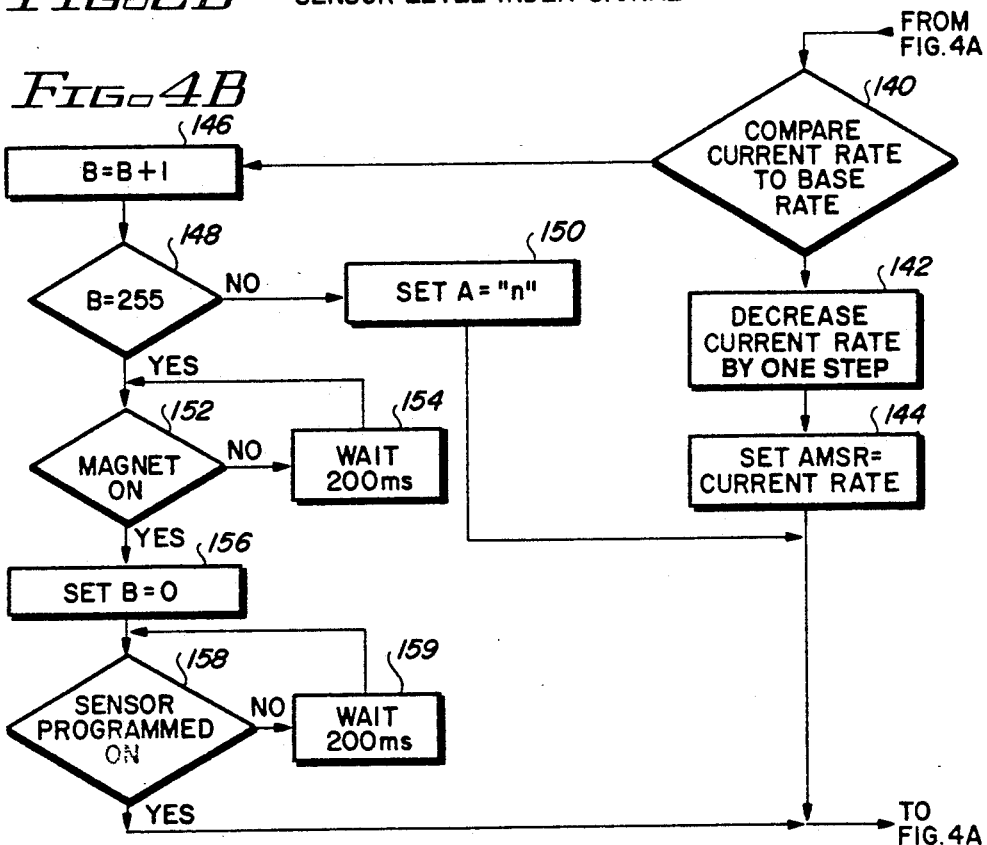
FIG. 4A and 4B show a diagram which teaches the preferred method for maintaining output amplitude at battery depletion in the rate responsive processor shown in FIG. 2A.
Figure 4A:
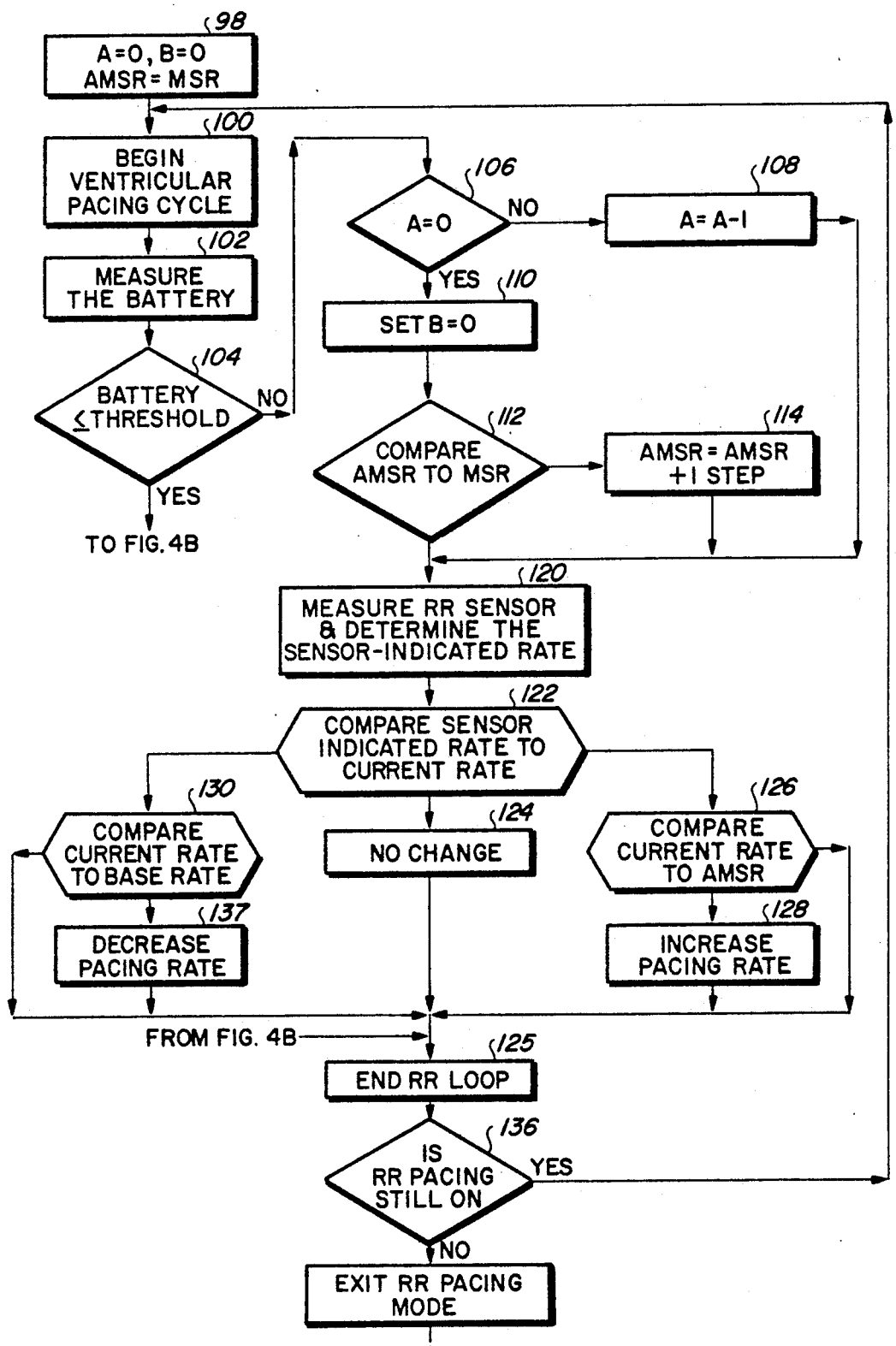

FIG. 4A and 4B describe this preferred embodiment, wherein FIG. 4A shows the steps taken when the battery is above threshold and FIG. 4B shows the steps taken when the battery is below threshold, and wherein like elements are numbered similarly as in FIG. 3.

In FIG. 4A, once RR programming has been turned ON, counters A and B are initialized to zero and the Allowable Maximum Sensor Rate (AMSR) is set equal to the programmed Maximum Sensor Rate (MSR) at step 98. A ventricular pacing cycle is initiated at 100. Following the stimulus, the battery is measured at 102. The battery voltage is compared to a predetermined threshold at step 104. If the battery voltage is above the predetermined threshold, then counter A is checked for "n" consecutive events, i.e., when the counter is zero at step 106. If the counter A is not at zero (which only occurs after at least one measurement below the predetermined threshold and is described in conjunction with FIG. 4B), then counter A is decremented at 108. If "n" consecutive events have occurred, then counter B is reset to zero at 110. The purpose of counter B is described below in conjunction with FIG. 4B.

At 112 the AMSR is compared to the programmed MSR. If they are equal, as is the case at BOL, the RR sensor is measured at 120 and rate responsive pacing continues as described in FIG. 3. If they are not equal (which only occurs after at least one measurement below the predetermined threshold and is described in conjunction with FIG. 4B), the AMSR will gradually be incremented towards the MSR at step 114, that is, if the battery voltage is above the predetermined threshold for "n" consecutive cycles, the Allowable Maximum Sensor Rate is adjusted toward the (programmed) Maximum Sensor Rate.

In FIG. 4B, the steps are shown for a battery measurement which is below threshold. The current rate is compared to the Base Rate at 140. If the current rate is greater than the Base Rate, then the current rate is decremented by at least one step at 142 and the AMSR is set equal to the new current rate at 144.

If the current rate is equal to the Base Rate, then counter B is incremented at 146. If, at 148, counter B is less than 255 (or some other desired number of counts), then counter A is set to "n" at 150, thus beginning the search for "n" consecutive battery measurements above threshold. In the preferred embodiment, "n" is set to two. If counter B is equal to 255 counts, then the pacemaker waits for a magnet to be applied at steps 152 and 154, effectively suspending rate responsive pacing. Once the magnet is applied, counter B is reset to zero at 156 and the pacemaker waits for a reprogramming signal from the external programmer at step 158 and 159.

It may therefore be appreciated by anyone skilled in the art that the invention can be extended to any pacemaker having a high current drain mode and successively lower current drain modes of operation. High current drain modes include rate responsive pacing, automatic capture verification, automatic amplitude adjustment, automatic sensitivity adjustment, telemetry transmission of ECG data or measurements, waveform analysis, tachycardia or arrhythmia recognition, or any other features which increase microprocessor processing time. The pacemaker of the present invention would include a means for switching from a high current drain mode to a successively lower current drain mode whenever the battery threshold detector indicates that the battery voltage is below a prescribed threshold. Low current drain modes would be achieved by altering or limiting parameters such as reducing the sampling rate, pacing rate, or otherwise reducing the duty cycle of the microprocessor.

Furthermore, the present invention may incorporate a plurality of thresholds such that these high current drain features may be switched to lower current drain modes according to a predetermined priority based on basic life support and quality of life.

It may thus be appreciated from the above detailed description that the advantages of the present invention result in extending the longevity of the pacemaker while providing a higher quality of life for the patient for as long as possible, making the method of the present invention a highly desirable enhancement to implantable cardiac pacemaker therapy.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. An implantable pacemaker, comprising:
a battery having a battery voltage which is dependent on current drain from the battery;
a battery voltage threshold detector for detecting when the battery voltage drops at least to a first predetermined voltage;
a pulse generator for generating stimulation pulses to a patient's heart, the pulse generator including means to generate constant amplitude stimulation pulses for a time period corresponding to the battery voltage being above the first predetermined voltage, the pulse generator further having means to operate in a plurality of modes of operation;
means for programming a plurality of parameters which control the pulse generator, the plurality of parameters including a first parameter corresponding to stimulation pulse amplitude and a second parameter which controls the pulse generator in a desired mode of operation, the second parameter having a plurality of values corresponding to a plurality of current drain levels; and
means for adjusting the second parameter to a value corresponding to a lower level of current drain when the battery voltage threshold detector detects that the battery voltage is below the first predetermined voltage.

2. The implantable pacemaker as recited in claim 1, wherein:
the plurality of parameters programmed by the programming means includes a base rate and a maximum rate of stimulation pulses;
the second parameter is stimulation rate;
the pacemaker includes a physiological sensor for producing a raw sensor signal indicative of physiological need; and
the adjusting means includes rate responsive processing means for processing the raw sensor signal and producing a sensor-indicated rate signal as an output, the rate responsive processing means including means for varying the stimulation rate between the base rate and the maximum rate of stimulation pulses in accordance with the sensor-indicated rate signal whenever the battery voltage is detected above the first predetermined voltage.

3. The implantable pacemaker as recited in claim 1, wherein:
the adjusting means includes means for adjusting the second parameter until either the battery voltage rises above the first predetermined voltage or a minimum value of the second parameter is reached, thereby extending the time period at which the pulse generator generates constant amplitude stimulation pulses.

4. The implantable pacemaker as recited in claim 1, wherein:
the second parameter is sampling rate;
the pacemaker includes sensing means for sensing cardiac signals waveforms; and
the adjusting means includes waveform analysis processing means for analyzing the cardiac signal waveforms when the battery voltage is detected above the first predetermined voltage.

5. An implantable stimulation device, comprising:
a battery having a battery voltage which is dependent on current drain from the battery;
a battery voltage threshold detector for detecting when the battery voltage drops at least to a first predetermined voltage;
a pulse generator for generating stimulation pulses to a patient's heart, the pulse generator having means to operate in a plurality of modes of operation including a signal processing mode of operation, the pulse generator further having means to generate constant amplitude stimulation pulses for a time period corresponding to the battery voltage being above the first predetermined voltage;
a signal processor for controlling the signal processing mode of operation, the signal processing mode of operation having at least a first and a second level of current drain, the first level of current drain being higher than the second level of current drain; and
means for switching the signal processing mode of operation from the first level of current drain to the second level of current drain when the battery voltage threshold detector detects that the battery voltage is below the first predetermined voltage.

6. The device as recited in claim 5, wherein:
the signal processor includes means for operating the signal processing mode of operation in a plurality of current drain levels, each successive current drain level being progressively lower in current drain than the previous level of current drain; and
the switching means includes means for switching the signal processing mode of operation from the second level of current drain to a progressively lower level of current drain each time the battery voltage threshold detector detects that the battery voltage is below the first predetermined voltage until either the battery voltage rises above the first predetermined voltage or a minimum level of current drain is reached, thereby extending the time period at which the pulse generator generates constant amplitude stimulation pulses.

7. The device as recited in claim 6, wherein:
the device includes a physiological sensor for producing a raw sensor signal indicative of physiological need, and means for programming a base rate and a maximum rate of stimulation pulses; and
the signal processor includes rate responsive processing means for processing the raw sensor signal and producing a physiologically-indicated rate signal as an output, the rate responsive processing means including means for varying the rate of stimulation pulses in accordance with the physiologically-indicated rate signal whenever the battery voltage is detected above the first predetermined voltage, wherein the signal processing mode of operation having a plurality of current draining levels is a rate responsive pacing mode having a plurality of stimulation rates, the plurality of stimulation rates being progressively lower in stimulation rate corresponding to progressively lower current drain levels.

8. The device as recited in claim 6, wherein:
the device includes sensing means for sensing cardiac signals waveforms; and the signal processor includes means for analyzing the cardiac signal waveforms for abnormalities thereof, the analyzing means including means for controlling a waveform analysis mode having a plurality of sampling rates, wherein the signal processing mode of operation having a plurality of current drain levels is the waveform analysis mode having a plurality of progressively lower sampling rates.

9. An implantable rate responsive pacemaker, comprising:
 a battery having a battery voltage which is dependent on current drain from the battery;
 a battery voltage threshold detector for detecting when the battery voltage drops at lest to a first threshold voltage;
 a sensor for sensing physiological need of a patient and for generating a raw sensor signal in response thereto;
 processing means for generating a sensor-indicated rate signal based n the raw sensor signal as sensed by the sensor;
 a pulse generator for generating stimulation pulses according to the sensor-indicated rate signal generated by the processing means; and
 means for decreasing and sensor-indicated rate signal when the battery voltage threshold detector detects that the battery voltage is below the first threshold voltage.

10. The implantable rate responsive pacemaker as recited in claim 9, wherein:
 the pacemaker includes means for determining a rate limit; and
 the decreasing means includes means for repeatedly decreasing the sensor-indicated rate signal until either the battery voltage rises above the first threshold voltage or the rate limit is reached.

11. The implantable rate responsive pacemaker as recited in claim 10, wherein:
 the pacemaker includes means for programming a base rate and a maximum rate of stimulation pulses; and
 the sensor-indicated rate signal generated by the processing means has a value between the base rate and the maximum rate of stimulation pulses when the battery voltage is above the first threshold voltage.

12. The implantable rate responsive pacemaker as recited in claim 11, wherein:
 the rate limit is equal to the base rate of stimulation pulses.

13. The implantable rate responsive pacemaker as recited in claim 11, wherein the rate limit is a rate lower than the base rate of stimulation pulses.

14. The implantable rate responsive pacemaker as recited in claim 11, wherein the processing means further comprises:
 means for comparing the sensor-indicated rate signal to the base rate signal whenever the battery voltage threshold detector detects that the battery voltage is at or below the first threshold voltage;
 means for counting the number of occurrences in which the sensor-indicated rate signal is equal to the base rate signal; and
 means for suspending rate responsive processing when the number is equal to a predetermined value.

15. The implantable rate responsive pacemaker as recited in claim 10, wherein:
 the battery has a first voltage and a second voltage associated therewith, the first voltage corresponding to battery end of life, the second voltage corresponding to battery recommended replacement time; and
 the first threshold voltage is equal to the second voltage.

16. An implantable rate responsive pacemaker as recited in claim 4, the pacemaker further including means for providing a programmable base rate signal and a programmable maximum rate signal, wherein the processing means comprises:
 means for generating an allowable maximum sensor rate signal, the allowable maximum sensor rate signal having a value between the programmable base rate signal and the programmable maximum sensor rate signal; and
 means for limiting the sensor-indicated rate signal to the programmable maximum sensor rate signal prior to detecting the battery voltage below the first threshold value and for limiting the sensor-indicated rate signal to the allowable maximum sensor rate signal after the battery voltage is detected below the first threshold value.

17. The implantable rate responsive pacemaker as recited in claim 16, wherein the means for generating an allowable maximum sensor rate signal comprises:
 means for periodically monitoring the battery voltage threshold detector to determine whether the battery voltage has dropped at least to the first threshold voltage;
 means for adjusting the allowable maximum sensor rate signal towards the programmable base rate signal whenever the monitoring means indicates at least once that the battery voltage threshold detector has detected the battery voltage at or below the first threshold voltage; and
 means for adjusting the allowable maximum sensor rate signal towards the programmable maximum sensor rate signal whenever the monitoring means indicates at least a prescribed number of consecutive times that the battery threshold detector has detected the battery voltage above the first threshold voltage.

18. The implantable rate responsive pacemaker as recited in claim 17, wherein the prescribed number of consecutive times that the battery threshold detector has detected the battery voltage above the first threshold voltage is at least two.

19. An implantable stimulating device, comprising:
 a battery having a battery voltage which is dependent on current drain from the battery;
 a plurality of battery voltage threshold detectors for detecting when the battery voltage drops to a selected one of a plurality of voltage thresholds;
 a pulse generator for generating stimulation pulses to a patient's heart, the pulse generator having means to generate constant amplitude stimulation pulses for a time period corresponding to the battery voltage being above a first predetermined voltage;
 a processor for controlling the operation of the pulse generator in a plurality of signal processing modes of operation, each signal processing mode of operation having at least two progressively lower current drain levels;

means for selecting one of the plurality of voltage thresholds for a desired signal processing mode of operation; and means for successively switching the desired signal processing mode of operation to one of the progressively lower current drain levels whenever the battery threshold detector detects that the battery voltage is below the selected voltage threshold.

20. A method of maintaining a constant stimulation pulse amplitude as the battery approaches depletion and for preventing rapid depletion of the battery in a rate responsive pacemaker, comprising the steps of:

sensing physiologic need of a patient with a physiologic sensor;

generating a physiologic sensor voltage from the physiologic sensor;

processing the physiologic sensor voltage to generate a sensor-indicated rate signal;

detecting when the voltage level of the battery drops below a predetermined threshold;

generating constant amplitude stimulation pulses at the sensor-indicated rate signal when the voltage level of the battery s above the predetermined threshold; and decreasing the sensor-indicated rate signal whenever the voltage level of the battery is below the predetermined threshold until either the battery voltage is above the predetermined threshold or the sensor-indicated rate signal is dropped to a minimum rate.

21. A method of maintaining a constant stimulation pulse amplitude as the battery in an implantable stimulation device, comprising the steps of:

detecting a voltage threshold across the battery;

generating constant amplitude stimulation pulses when the battery is above the voltage threshold;

operation the implantable stimulation device in a signal processing mode of operation, the signal processing mode of operation having at least two progressively lower current drain levels; and switching the signal processing mode of operation to a progressively lower current draining level each time the batter voltage is detected below the voltage threshold.

22. A method of maintaining a consonant stimulation pulse amplitude as the battery approaches depletion and preventing rapid depletion of a battery in an implantable stimulation device, comprising the steps of:

generating constant amplitude stimulation pulses when the battery is above the voltage threshold;

operating the implantable stimulation device in a plurality of signal processing modes, each signal processing mode having at least two progressively lower current drain levels;

detecting when the voltage across the battery drops below a plurality of thresholds;

selecting one of the plurality of thresholds for each of the plurality of signal processing modes; and switching from one of the plurality of signal processing modes to one of the progressively lower current drain levels each time the battery voltage is detected below the selected one of the plurality of thresholds.

23. A method of maintaining a constant stimulation pulse amplitude as the battery approaches depletion and preventing rapid depletion of a battery in an implantable pacemaker, the method comprising the steps of:

operating the pacemaker in a plurality of modes of operation;

programming a plurality of parameters which control the pacemaker, the plurality of parameters including a first parameter corresponding to stimulation pulse amplitude and a second parameter which controls the pacemaker in a desired mode of operation, the second parameter having a plurality of values corresponding to a plurality of current drain levels;

detecting when the battery voltage drops to a first threshold;

generating constant amplitude stimulation pulses to a patient's heart when the battery voltage is above the first voltage; and adjusting the second parameter to a value corresponding to a progressively lower level of current drain whenever the battery voltage is below the first threshold.

* * * * *